US010893913B2

(12) United States Patent
Peine

(10) Patent No.: US 10,893,913 B2
(45) Date of Patent: Jan. 19, 2021

(54) ROBOTIC SURGICAL SYSTEMS WITH INDEPENDENT ROLL, PITCH, AND YAW SCALING

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 276 days.

(21) Appl. No.: 15/772,142

(22) PCT Filed: Dec. 8, 2016

(86) PCT No.: PCT/US2016/065588
§ 371 (c)(1),
(2) Date: Apr. 30, 2018

(87) PCT Pub. No.: WO2017/100434
PCT Pub. Date: Jun. 15, 2017

(65) Prior Publication Data
US 2018/0310999 A1     Nov. 1, 2018

Related U.S. Application Data

(60) Provisional application No. 62/265,457, filed on Dec. 10, 2015.

(51) Int. Cl.
*A61B 34/30*     (2016.01)
*A61B 34/00*     (2016.01)
(Continued)

(52) U.S. Cl.
CPC .............. *A61B 34/30* (2016.02); *A61B 34/10* (2016.02); *A61B 34/37* (2016.02); *A61B 34/74* (2016.02);
(Continued)

(58) Field of Classification Search
None
See application file for complete search history.

(56) References Cited

U.S. PATENT DOCUMENTS 5,855,583 A * 1/1999 Wang ............... A61B 17/11
318/568.11
6,120,433 A * 9/2000 Mizuno ............... A61B 34/70
600/102
(Continued)

FOREIGN PATENT DOCUMENTS

KR    20120068597 A    6/2012
WO    2006056738 A1    6/2006
(Continued)

OTHER PUBLICATIONS

International Search Report dated Mar. 13, 2017 in PCT/US2016/065588.
(Continued)

*Primary Examiner* — Bhavesh V Amin

(57) ABSTRACT

A robotic surgical system includes a linkage, an input device, and a processing unit. The linkage moveably supports a surgical tool relative to a base. The input device is rotatable about a first axis of rotation and a second axis of rotation. The processing unit is in communication with the input device and is operatively associated with the linkage to rotate the surgical tool about a first axis of movement based on a scaled rotation of the input device about the first axis of rotation by a first scaling factor and to rotate the surgical tool about a second axis of movement based on a scaled rotation of the input device about the second axis of rotation by a second scaling factor that is different from the first scaling factor.

7 Claims, 3 Drawing Sheets

(51) Int. Cl.
  *A61B 34/37*   (2016.01)
  *A61B 34/10*   (2016.01)
  *A61B 90/00*   (2016.01)
  *B25J 9/16*    (2006.01)
  *B25J 11/00*   (2006.01)
  *G16H 50/50*   (2018.01)

(52) U.S. Cl.
  CPC ............. *A61B 34/77* (2016.02); *A61B 90/37* (2016.02); *B25J 9/1605* (2013.01); *B25J 11/008* (2013.01); *A61B 2034/102* (2016.02); *A61B 2090/371* (2016.02); *G16H 50/50* (2018.01)

(56) References Cited

U.S. PATENT DOCUMENTS

| | | | | |
|---|---|---|---|---|
| 6,298,278 | B1 * | 10/2001 | Pierse | G05B 19/401 29/37 A |
| 7,695,481 | B2 | 4/2010 | Wang et al. | |
| 7,741,802 | B2 * | 6/2010 | Prisco | B25J 9/1689 318/568.11 |
| 7,933,677 | B2 * | 4/2011 | Lankalapalli | G05B 19/409 700/172 |
| 8,768,516 | B2 * | 7/2014 | Diolaiti | A61B 34/30 700/262 |
| 8,828,023 | B2 * | 9/2014 | Neff | A61B 34/35 606/130 |
| 8,934,003 | B2 * | 1/2015 | Popovic | A61B 34/30 348/65 |
| 8,944,070 | B2 * | 2/2015 | Guthart | A61B 34/20 128/898 |
| 9,002,518 | B2 * | 4/2015 | Manzo | A61B 34/76 700/261 |
| 9,107,686 | B2 * | 8/2015 | Moon | A61B 34/77 |
| 9,205,564 | B2 * | 12/2015 | Popovic | G06T 7/246 |
| 9,417,621 | B2 * | 8/2016 | Diolaiti | G05B 19/402 |
| 9,687,310 | B2 * | 6/2017 | Nowlin | A61B 34/71 |
| 9,770,300 | B2 * | 9/2017 | Kwon | A61B 34/30 |
| 9,775,678 | B2 * | 10/2017 | Lohmeier | A61B 34/76 |
| 9,782,225 | B2 * | 10/2017 | Lohmeier | A61B 34/30 |
| 10,117,714 | B2 * | 11/2018 | Nowlin | A61B 34/37 |
| 10,117,715 | B2 * | 11/2018 | Lohmeier | A61B 17/00 |
| 10,123,844 | B2 * | 11/2018 | Nowlin | A61B 90/37 |
| 10,194,998 | B2 * | 2/2019 | Nowlin | A61B 34/71 |
| 10,258,421 | B2 * | 4/2019 | Lohmeier | A61B 34/76 |
| 10,390,900 | B2 * | 8/2019 | Lohmeier | A61B 34/30 |
| 10,675,050 | B2 * | 6/2020 | Staunton | A61B 17/32002 |
| 2007/0151389 | A1 * | 7/2007 | Prisco | A61B 34/70 74/490.05 |
| 2007/0260115 | A1 * | 11/2007 | Brock | A61B 34/77 600/114 |
| 2008/0140257 | A1 * | 6/2008 | Sato | B25J 9/1638 700/258 |
| 2008/0215065 | A1 * | 9/2008 | Wang | A61B 34/75 606/130 |
| 2008/0295564 | A1 * | 12/2008 | Kaneko | G05B 19/4061 72/405.13 |
| 2009/0030429 | A1 * | 1/2009 | Madhani | B25J 9/1697 606/130 |
| 2009/0088775 | A1 * | 4/2009 | Swarup | A61B 34/30 606/130 |
| 2009/0227925 | A1 * | 9/2009 | McBean | A61F 5/0127 602/16 |
| 2010/0332033 | A1 * | 12/2010 | Diolaiti | B25J 9/1689 700/259 |
| 2014/0094968 | A1 * | 4/2014 | Taylor | B25J 3/04 700/257 |
| 2014/0142592 | A1 * | 5/2014 | Moon | A61B 34/37 606/130 |
| 2014/0343730 | A1 * | 11/2014 | Kim | B25J 9/1625 700/262 |
| 2015/0018841 | A1 * | 1/2015 | Seo | A61B 34/30 606/130 |
| 2015/0066051 | A1 * | 3/2015 | Kwon | A61B 34/30 606/130 |
| 2016/0135909 | A1 * | 5/2016 | Ogawa | A61B 34/37 606/130 |
| 2016/0229052 | A1 * | 8/2016 | Touma | B25J 9/161 |
| 2017/0224428 | A1 * | 8/2017 | Kopp | A61B 34/30 |
| 2018/0014897 | A1 * | 1/2018 | Peine | A61B 34/77 |
| 2018/0310999 | A1 * | 11/2018 | Peine | A61B 34/74 |

FOREIGN PATENT DOCUMENTS

| | | |
|---|---|---|
| WO | 2013018983 A1 | 2/2013 |
| WO | 2016053657 A1 | 4/2016 |
| WO | 2016133633 A1 | 8/2016 |

OTHER PUBLICATIONS

International Preliminary Report on Patentability dated Jun. 12, 2018 in PCT/US2016/065588.

Extended European Search Report dated Oct. 22, 2019 corresponding to counterpart Patent Application EP 16873838.3.

Partial Supplementary European Search Report dated Jul. 16, 2019 corresponding to counterpart Patent Application EP 16873838.3.

Chinese First Office Action dated Jun. 12, 2020 corresponding to counterpart Patent Application CN 201680071848.0.

* cited by examiner

ROBOTIC SURGICAL SYSTEMS WITH INDEPENDENT ROLL, PITCH, AND YAW SCALING

CROSS-REFERENCE TO RELATED APPLICATIONS

This application is a U.S. National Stage Application filed under 35 U.S.C. § 371(a) of International Patent Application Serial No. PCT/US2016/065588, filed Dec. 8, 2016, which claims the benefit of and priority to U.S. Provisional Patent Application Ser. No. 62/265,457, filed Dec. 10, 2015, the entire disclosure of which is incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

Robotic surgical systems typically used a scaling factor to scale down the motions of the surgeons hands to determine the desired position of the end effector within the patient so that the surgeon could more precisely move the end effector inside the patient. However, the larger the scaling factor, the farther the surgeon had to move the input device handle to move the end effector the same distance. Since the input device handle has a fixed range of motion, this meant that for larger scaling factors the surgeon may have reached an end of the range of motion of an input handle more often.

In addition, during a medical procedure a surgeon needs to rotate the end effector about a roll axis, a pitch axis, and a yaw axis to properly position the end effector to act on tissue. Typically, rotation about the roll, pitch, and yaw (RPY) axes of the input device handle is not scaled to rotation of the end effector about the RPY axes.

There is a need for robotic surgical system that is able to scale input handle rotations of the surgeon during robotic surgical procedures.

SUMMARY

This disclosure generally relates to the scaling of movement of an input device of a user interface to movement of a tool of a robotic system during a surgical procedure. In an aspect of the present disclosure, a robotic surgical system includes a linkage, an input device, and a processing unit. The linkage moveably supports a surgical tool relative to a base. The input device is rotatable about first and second axes of rotation. The processing unit is in communication with the input device. The processing unit is also operatively associated with the linkage to rotate the surgical tool about a first axis of movement based on a scaled rotation of the input device about the first axis of rotation by a first scaling factor and to rotate the surgical tool about a second axis of movement based on a scaled rotation of the input device about the second axis of rotation by a second scaling factor that is different from the first scaling factor.

In aspects, the second scaling factor is less than the first scaling factor. The first scaling factor may be about 1.0.

In some aspects, the input device is rotatable about a third axis of rotation. The processing unit may be operatively associated with the linkage to rotate the surgical tool about a third axis of movement based on scaled rotation of the input device about the third axis of rotation by a third scaling factor. The first, second, and third scaling factors may be equal to one another, may each be different from one another, or two of the scaling factors may be equal to one another and different from the other scaling factor. For example, the second scaling factor may be less than the first scaling factor and the third scaling factor may be greater than the first scaling factor.

In another aspect of the present disclosure, a robotic surgical system includes a linkage, an input device, and a processing unit. The linkage moveably supports a surgical tool relative to a base. The input device is rotatable about a first axis of rotation. The input device is rotatable from an idle position in a first input direction about the first axis of rotation towards a first rotated position. The processing unit is in communication with the input device and is operatively associated with the linkage to rotate the surgical tool about a first axis of movement in a first output direction when the input device is rotated from the idle position towards the first rotated position and to maintain a radial position of the surgical tool about the first axis of movement when the input device is in the idle position.

In aspects, the processing unit varies a radial speed of the surgical tool about the first axis of movement based on an amount of rotation of the input device from the idle position towards the first rotated position. The processing unit may vary the radial speed of the surgical tool about the first axis of movement in at least one of a smooth or stepped manner.

In some aspects, the input device is rotatable about the first axis of rotation in a second direction opposite the first direction towards a second rotated position. The processing unit may be operatively associated with the linkage to rotate the surgical tool about the first axis of movement in a second output direction opposite the first output direction when the input device is rotated from the idle position towards the second rotated position.

In particular aspects, the input device is rotatable about a second axis of rotation. The processing unit is operatively associated with the linkage to rotate the surgical tool about a second axis of movement based on a scaled rotation of the input device about the second axis of rotation by a first scaling factor. The input device may be rotatable about a third axis of rotation. The processing unit may be operatively associated with the linkage to rotate the surgical tool about a third axis of movement based on a scaled rotation of the input device about the third axis of rotation by a second scaling factor. The first scaling factor may be different from the first scaling factor.

In another aspect of the present disclosure, a method of operating a surgical robot includes rotating an input device of a robotic surgical system about a first axis of rotation and rotating the input device about a second axis of rotation. Rotating the input device about the first axis of rotation includes rotating the input device a first input distance to rotate a tool of a robotic surgical system about a first axis of movement a first output distance. The first input distance scaled to the first output distance by a first scaling factor. Rotating the input device about the second axis of rotation includes rotating the input device a second input distance to rotate the tool about a second axis of movement a second output distance. The second input distance scaled to the second output distance by a second scaling factor that is different from the first scaling factor.

In aspects, the method includes rotating the input device about a third axis of rotation a third input distance to rotate the tool about a third axis of movement a third output distance. The third input distance may be scaled to the third output distance by a third scaling factor that is different from the first scaling factor. The third scaling factor may also be different from the second scaling factor.

In another aspect of the present disclosure, a method of operating a surgical robot includes rotating an input device of a robotic surgical system about a first axis of rotation in a first input direction from an idle position to a first rotated position to rotate a tool of a robotic surgical system about a first axis of movement in a first output direction at a first output velocity and returning the input device to the idle position to stop rotation of the tool about the first axis of movement.

In aspects, the method includes rotating the input device about the first axis of rotation in the first input direction to a second rotated position beyond the first rotated position to rotate the tool about the first axis of movement in the first output direction at a second output velocity greater than the first output velocity.

In some aspects, the method includes rotating the input device about the first axis of rotation in a second input direction opposite the first input direction from the idle position to a third rotated position to rotate the tool about the first axis of movement in a second output direction opposite the first output direction at the first output velocity.

In an aspect of the present disclosure, a robotic surgical simulator includes a virtual linkage, an input device, and a processing unit. The virtual linkage virtually supports a virtual surgical tool relative to a virtual base. The input device is rotatable about first and second axes of rotation. The processing unit is in communication with the input device. The processing unit is also operatively associated with the virtual linkage to rotate the virtual surgical tool about a first axis of movement based on a scaled rotation of the input device about the first axis of rotation by a first scaling factor on a display of the user interface and to virtually rotate the virtual surgical tool about a second axis of movement based on a scaled rotation of the input device about the second axis of rotation by a second scaling factor that is different from the first scaling factor on the display.

In another aspect of the present disclosure, a robotic surgical simulator includes a virtual linkage, an input device, and a processing unit. The virtual linkage virtually supports a virtual surgical tool relative to a virtual base. The input device is rotatable about a first axis of rotation. The input device is rotatable from an idle position in a first input direction about the first axis of rotation towards a first rotated position. The processing unit is in communication with the input device and is operatively associated with the virtual linkage to rotate the virtual surgical tool about a first axis of movement in a first output direction on a display when the input device is rotated from the idle position towards the first rotated position and to maintain a radial position of the virtual surgical tool about the first axis of movement on the display when the input device is in the idle position.

In another aspect of the present disclosure, a method of simulating a surgical procedure includes rotating an input device of a robotic surgical system about a first axis of rotation and rotating the input device about a second axis of rotation. Rotating the input device about the first axis of rotation includes rotating the input device a first input distance to rotate a virtual tool of a robotic surgical system about a first axis of movement a first output distance. The first input distance scaled to the first output distance by a first scaling factor. Rotating the input device about the second axis of rotation includes rotating the input device a second input distance to rotate the virtual tool about a second axis of movement a second output distance. The second input distance scaled to the second output distance by a second scaling factor that is different from the first scaling factor.

In aspects, the method includes rotating the input device about a third axis of rotation a third input distance to rotate the virtual tool about a third axis of movement a third output distance. The third input distance may be scaled to the third output distance by a third scaling factor that is different from the first scaling factor. The third scaling factor may also be different from the second scaling factor.

Further details and aspects of exemplary embodiments of the present disclosure are described in more detail below with reference to the appended figures.

BRIEF DESCRIPTION OF THE DRAWINGS

Various aspects of the present disclosure are described herein below with reference to the drawings, which are incorporated in and constitute a part of this specification, wherein.

DETAILED DESCRIPTION

Figure 1:
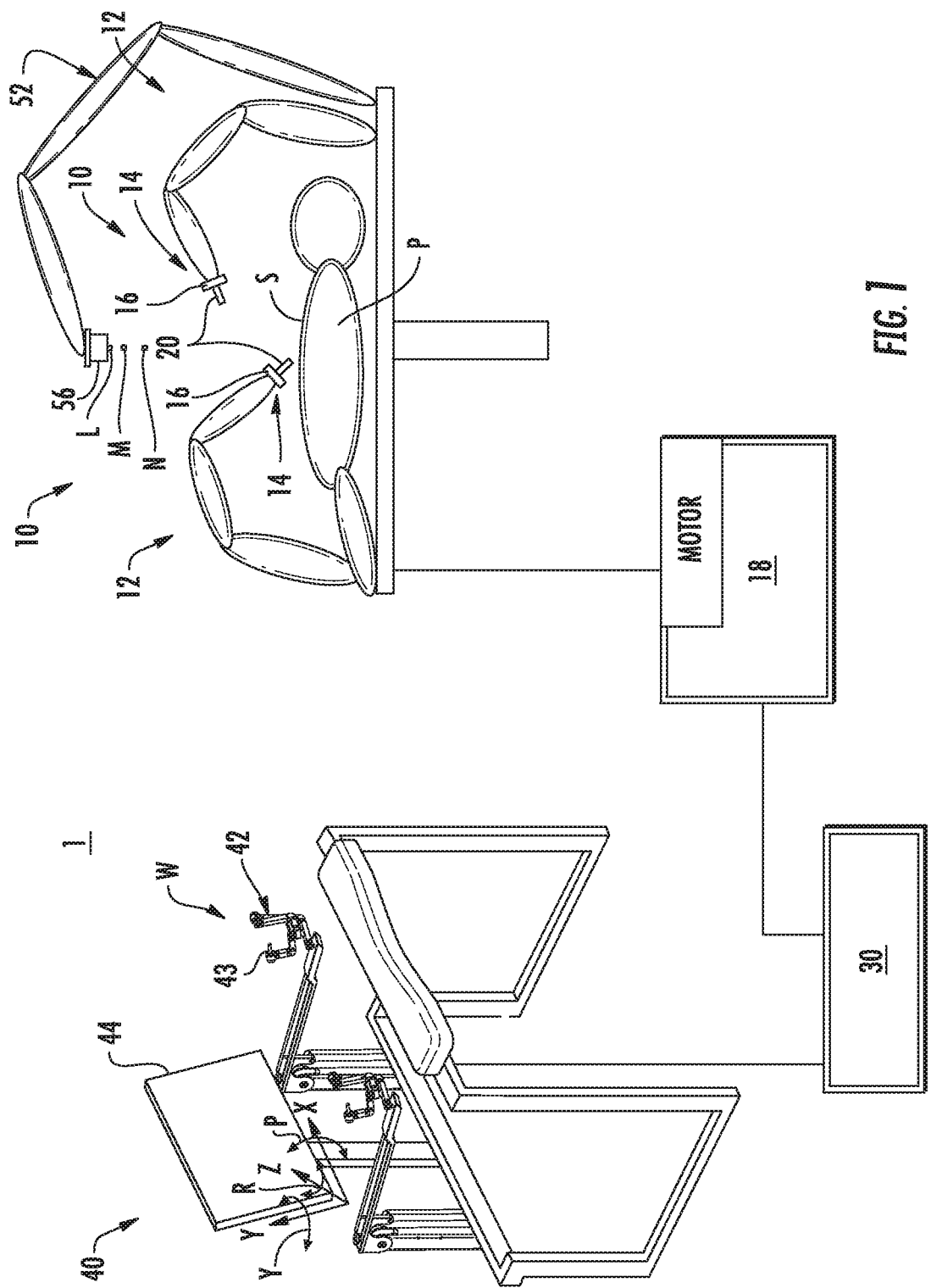
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician. In addition, as used herein the term "neutral" is understood to mean non-scaled.

This disclosure generally relates to the scaling of movement of an input device of a user interface to movement of a tool of a robotic system during a surgical procedure. In particular, this disclosure relates to the scaling of movement about a roll axis, a pitch axis, and a yaw axis. The scaling about each of these axes may be positive (i.e., increase the movement of the tool with respect to movement of the input device), negative (i.e., decrease the movement of the tool with respect to movement of the input device), or neutral (i.e., equal to the movement of the tool with respect to movement of the input device). The scaling of the movement in a positive manner may allow a clinician to have increased dexterity from what is allowed by human anatomy. For example, when a wrist action (e.g., about the roll axis) is scaled in a positive manner, a clinician may be able to rotate a tool a full rotation in each direction with a quarter rotation of the wrist of the clinician.

Referring to FIG. 1, a robotic surgical system 1 in accordance with the present disclosure is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the arms 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which are supported on control arms 43 which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include input devices 46 (FIG. 2) which allow the surgeon to manipulate (e.g., clamp, grasp, fire, open, close, rotate, thrust, slice, etc.) the tools 20 supported at the ends 14 of the arms 12.

Figure 2:
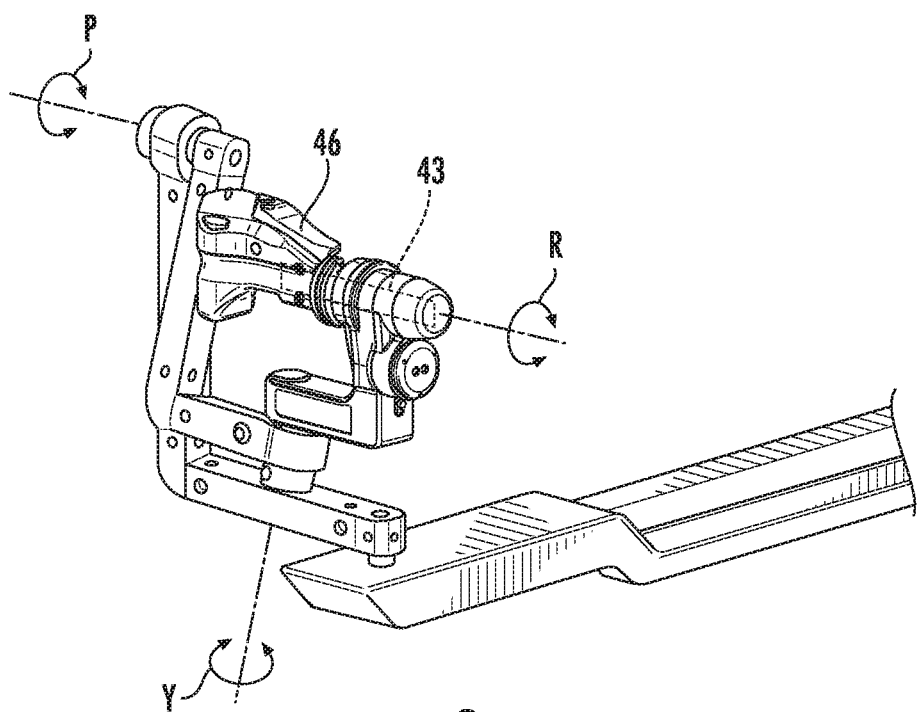
FIG. 2 is a perspective view of a input device supported on an end of a control arm of the user interface of FIG. 1.

With additional reference to FIG. 2, each of the input handles 42 is moveable through a predefined workspace to move the ends 14 of the arms 12, e.g., tools 20, within a surgical site "S". The three-dimensional images on the display device 44 are orientated such that the movement of the input handles 42 move the ends 14 of the arms 12 as viewed on the display device 44. The three-dimensional images remain stationary while movement of the input handles 42 is scaled to movement of the ends 14 of the arms 12 within the three-dimensional images. To maintain an orientation of the three-dimensional images, kinematic mapping of the input handles 42 is based on a camera orientation relative to an orientation of the ends 14 of the arms 12. It will be appreciated that the orientation of the three-dimensional images on the display device may be mirrored or rotated relative to view from above the patient "P". In addition, it will be appreciated that the size of the three-dimensional images on the display device 44 may be scaled to be larger or smaller than the actual structures of the surgical site permitting a clinician to have a better view of structures within the surgical site "S". As the input handles 42 are moved, the tools 20 are moved within the surgical site "S" as detailed below. As detailed herein, movement of the tools 20 may also include movement of the ends 14 of the arms 12 which support the tools 20.

For a detailed discussion of the construction and operation of a robotic surgical system 1, reference may be made to U.S. Pat. No. 8,828,023, the entire contents of which are incorporated herein by reference.

As detailed above, the user interface 40 is in operable communication with the robotic system 10 to perform a surgical procedure on a patient; however, it is envisioned that the user interface 40 may be in operable communication with a surgical simulator (not shown) to virtually actuate a robotic system and/or tool in a simulated environment. For example, the surgical robot system 1 may have a first mode where the user interface 40 is coupled to actuate the robotic system 10 and a second mode where the user interface 40 is coupled to the surgical simulator to virtually actuate a robotic system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the input handles 42, the surgical simulator moves representative tools that are virtually acting on tissue. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

The movement of the tools 20 is scaled relative to the movement of the input handles 42. When the input handles 42 are moved within a predefined workspace, the input handles 42 send control signals to the processing unit 30. The processing unit 30 analyzes the control signals to move the tools 20 in response to the control signals. The processing unit 30 transmits scaled control signals to the robot base 18 to move the tools 20 in response to the movement of the input handles 42. The processing unit 30 scales the control signals by dividing an Input$_{distance}$ (e.g., the distance moved by one of the input handles 42) by a scaling factor $S_F$ to arrive at a scaled Output$_{distance}$ (e.g., the distance that one of the ends 14 is moved). The scaling factor $S_F$ is in a range between about 1 and about 10 (e.g., 3). This scaling is represented by the following equation:

$$\text{Output}_{distance} = \text{Input}_{distance}/S_F$$

It will be appreciated that the larger the scaling factor $S_F$ the smaller the movement of the tools 20 relative to the movement of the input handles 42.

For a detailed description of scaling movement of the input handle 42 along the X, Y, and Z coordinate axes to movement of the tool 20, reference may be made to commonly owned International Patent Application Serial No. PCT/US2015/051130, filed on Sep. 21, 2015, and entitled "Dynamic Input Scaling for Controls of Robotic Surgical System," and International Patent Application No. PCT/US2016/14031, filed Jan. 20, 2016, the entire contents of each of these disclosures is herein incorporated by reference.

Figure 3:
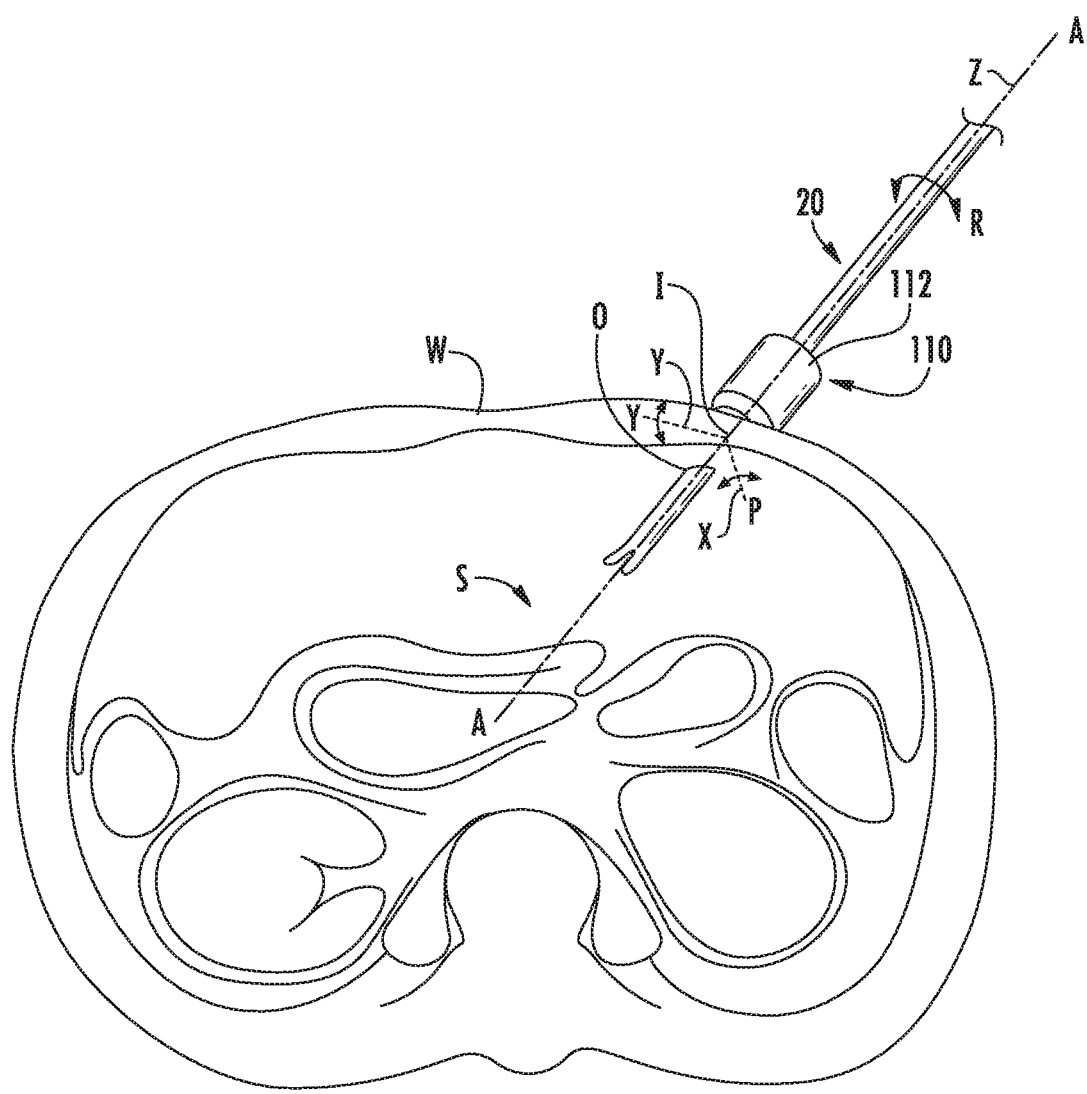
FIG. 3 is a cutaway view of a body cavity of a patient showing a tool of the robotic surgical system of FIG. 1 inserted in the body cavity.

Referring also to FIGS. 2 and 3, the rotation of the input device 46 relative to each of the X, Y, and Z coordinate axes may be scaled to rotation of the tool 20 about a roll axis "R", a pitch axis "P", and a yaw axis "Y" (RPY). It will be appreciated that RPY axes are orientated to the camera frame as displayed on the display device 44 such that motions of the handles 42 and/or input device 46 are relative to a clinician's view of the display device 44. Specifically, the roll axis "R" is about the Z coordinate axis, the pitch axis "P" is about the X coordinate axis, and the yaw axis "Y" is about the Y coordinate axis. The scaling of rotation of the input device 46 about each of the RPY axes may be scaled in a positive, negative, or neutral manner. By scaling rotation in a positive manner, a clinician is able to reduce rotation of the input device 46 about a particular one of the RPY axes to achieve a desired rotation of the tool 20 about the respective RPY axis. This positive scaling may allow a clinician to have dexterity beyond a natural movement of the human body. For example, a clinician may roll a tool 20 beyond what is possible with the movement of the clinician's wrist without releasing the input device 46. In contrast, by scaling rotation in a negative manner, a clinician is able to more precisely control rotation of the tool 20 about a particular one of the RPY axes of the tool 20 in response to rotation of the input device 46.

Rotation of the input device 46 about each of the RPY axes may be scaled in a different manner to rotation of the tool 20. For example, rotation of the input device 46 about the control shaft 43, i.e., rotation about the roll axis "R", may be scaled in a positive manner, rotation of the input device 46 about the pitch axis "P" may be scaled in a neutral manner, and rotation of the input device 46 about the yaw axis "Y" may be scaled in a negative manner. Any other combinations of scaling are contemplated herein and form a part of the present disclosure.

Rotation of the tool 20 is scaled in response to rotation of the input device 46 about a respective one of the RPY axes. The movement about the respective RPY axis is measured in degrees which are scaled by a scaling factor $S_F$ similar to movement along the XYZ coordinate axes as detailed above. Continuing the example above, with rotation about the roll axis "R" scaled in a positive manner, a roll scaling factor $RS_F$ is less than 1.0, e.g., in a range of about 0.10 to about 0.95, such that an Output$_{angle}$ is greater than an Input$_{angle}$ about the roll axis "R". In addition, with rotation about the pitch axis "P" scaled in a neutral manner, a pitch scaling factor $PS_F$ is equal to about 1.0 such that an Output$_{angle}$ is equal to an Input$_{angle}$ about the pitch axis "P". Further, with rotation about the yaw axis "Y" scaled in a negative manner, a yaw scaling factor $YS_F$ is greater than 1.0, e.g., in a range of about 1.10 to about 10.0, such that an Output$_{angle}$ is less than an Input$_{angle}$ about the yaw axis "Y". It is contemplated that each of the RPY scaling factors $RS_F$, $PS_F$, and $YS_F$ may be equal to another one of the RPY scaling factor or each of the RPY scaling factors may be different from one another.

Additionally or alternatively, one of the RPY scaling factors may be varied as the input device 46 is rotated about a respective one of the RPY axes from an idle position to a limit of movement about the respective RPY axis. For example, as the input device 46 is rotated from an idle position (FIG. 2) about the roll axis "R", the roll scaling factor $RS_F$ is initially about 1.0 and decreases to a roll scaling factor $RS_F$ of about 0.5 as the input device 46 approaches a limit of rotation about the roll axis "R". This varying of the roll scaling factor $RS_F$ may be in a linear manner, an exponential manner, or a functional manner. Further, the varying of the roll scaling factor $RS_F$ may be in a first manner (e.g., fixed, linear, exponential, or functional) adjacent the idle position and be in a second manner (e.g., fixed, linear, exponential, or functional) adjacent the limit of rotation. The varying of the RPY scaling factors may be customizable for a clinician interfacing with the user interface 40 (FIG. 1) or a tool 20 (FIG. 1) attached to a respective linkage 12. Additionally or alternatively, varying of the RPY scaling factors may be dynamic during the surgical procedure such that a clinician or the processing unit 30 (FIG. 1) may vary the manner (e.g., positive, neutral, or negative) of one or more of the RPY scaling factors or the manner in varying the value (e.g., fixed, linear, exponential, or functional) of the one or more of the RPY scaling factors. For a detailed discussion of methods of varying a scaling factor as movement or rotation approaches a limit reference can be made to U.S. Provisional Patent Application No. 62/118,123, filed Feb. 19, 2015, and entitled "Repositioning Method of Input Device for Robotic Surgical System," the entire contents of which are incorporated herein by reference.

It is contemplated that one or more of the RPY scaling factors may be varied after swapping or switching tools (e.g., tool 20) attached to the end of an arm 12 to align the input device 46 with the tool when the tool is attached misaligned from the input device 46. Specifically, the RPY scaling factor in each direction may be more negative when the clinician moves the input handle 46 away from a centered or aligned position and may be more positive when the clinician moves the input handle 46 towards the centered or aligned position until the tool is aligned with the input device 46. When the tool is aligned with the input device 46, the RPY scaling factors return to operating in a symmetrical manner, positive, neutral, or negative.

In another embodiment of the present disclosure, the rotation of the tool 20 about the RPY axes may be throttled in response to the displacement of the input device 46 from an initial or idle position to a displaced or rotated position. In such embodiments, when the input device 46 is in the idle position as shown in FIG. 2, the tool 20 maintains its position relative to the RPY axes. As the input device 46 is rotated about a particular RPY axis, the tool 20 is rotated about the particular RPY axis in a direction related to the direction of rotation of the input device 46 at a constant velocity. For example, when the input device 46 is rotated from an idle position (FIG. 2) about the roll axis "R", the tool 20 initially rotates at an angular speed of about 1° a second. Additional rotation of the input device 46 about the roll axis "R" does not affect rotation of the tool 20. To stop rotation of the tool 20, the input device 46 is returned to the idle position. It is contemplated that the idle position may be a singular or zero degree position or may be a range of about −5° to about 5° of rotation such that when the input device 46 is rotated beyond the idle position, the tool 20 is rotated.

Alternatively, the velocity of the rotation of the tool 20 about the particular RPY axis may vary in response to angular displacement of the input device 46 about the particular RPY axis. For example, when the input device 46 is rotated from an idle position (FIG. 2) about the roll axis "R", the tool 20 initially rotates at an angular speed of about 1° a second and as the input device 46 approaches a limit of rotation about the roll axis "R" the angular speed of the tool rotating about the roll axis "R" increases to about 10° a second. The varying of the angular speed of rotation of the tool 20 may be linear, exponential, or functional in response to rotation of the input device 46 about the roll axis "R". Further, varying the angular speed of rotation of the tool 20 may be smooth or may be stepped.

As detailed below, a method for scaling the rotation of the tool 20 about the roll axis "R" is detailed below in accordance with the present disclosure. The method scales the orientation or rotation of the tool 20 based on the rotation of the input device or handle 46 in a world frame of the user interface 40. The orientation of the input handle 46 in the world frame is represented as $R_{orientation} = {}^{world}_{handle}R$. The processing unit 30 (FIG. 1) scales the rotation of the input handle 46 in the world frame as scaled $R_{scaled} = {}^{world}_{virtualhandle}R$ to increase the rotation of the tool 20 in response to rotation of the input handle 46. In a neutral orientation for the scaling, the input handle 46 is positioned such that its physical orientation matches the neutral orientation such that $R_{orientation} = {}_{handle}{}^{world}R = R_{scaled} = {}_{virtialhandle}{}^{world}R$.

The neutral orientation can be defined in the world frame as a matrix ${}_{neutral}{}^{world}R$ such that any orientation of the handle $R_{orientation}$ is relative to the neutral orientation as follows:

$$R_{orientation} = {}_{handle}{}^{world}R = {}_{neutral}{}^{world}R \cdot {}_{handle}{}^{neutral}R$$

The scaling S can then be applied to the ${}_{handle}{}^{neutral}R$ such that:

$$R_{scaled} = {}_{virutalhandle}{}^{world}R = {}_{neutral}{}^{world}R \cdot S[{}_{handle}{}^{neutral}R]$$

Combining the two expressions above yields:

$$R_{scaled} = {}_{neutral}{}^{world}R \cdot S[({}_{neutral}{}^{world}R)^{-1} \cdot R_{orientation}]$$

The scaling of rotation of the input handle 46 by a fixed scaling factor can be expressed as Euler rotation vectors such that a rotation vector "R" can be scaled by multiplying the rotation vector by a scalar "s" as:

$$S_1(s)[r] = sr$$

When the inputs and outputs are rotation matrices, conversions are necessary such that:

$$S_1(s)[R] = r2R[s \cdot R2r[R]]$$

with r2R[r] being the conversion of an Euler rotation vector "R" to a rotation matrix and R2r[R] being a conversion of a rotation matrix "R" to an Euler rotation vector.

The above expression may suffer from aliasing based on a rigid body rotation having one matrix representation but having an infinite number of rotation vector representations that differ in multiples of $2\pi$. If large rotations of the tool 20 are allowed, the conversion of the rotation vector may alias in different ways such that the same pose is mapped to a number of rotation vector values which may cause a discontinuity in the scaled output. To avoid discontinuities, the aliasing is removed from the rotation vector "R" by changing the magnitude by a multiple of $2\pi$ a so the rotation vector "R" matches the previous orientation. This anti-aliasing function can be represented as AA[r] such that the final expression is as follows:

$$S_1(s)[R] = r2R[s \cdot AA[R2r[R]]]$$

The scaling of the input handle 46 may also be specific to a given axis such that rotation about each axis is scaled in a different manner. For example, scaling about the pitch or yaw axes may be scaled in a different manner or separately from scaling about the roll axis. To separate the neutral scaling of individual axes, the relative orientation ${}_{handle}{}^{neutral}R$ is decomposed into a pitch and yaw component and a roll component such that ${}_{handle}{}^{neutral}R = R_{py} \cdot R_{roll}$. A uniform scaling can then be applied to each of the $R_{py}$ and $R_{roll}$ by converting each rotation to Euler rotation vectors and then scaling the angle. The pitch/yaw component $R_{py}$ can be scaled by a pitch/yaw scaling factor $S_{py}$ and the roll component $R_{roll}$ can be scaled by a roll scaling factor $S_{roll}$. It will be appreciated that rotations greater than $2\pi$ should be avoided to avoid aliasing as detailed above.

The separated scaling can be represented as:

$$R_{scaled} = {}_{neutral}{}^{world}R \cdot S_1(S_{py})[R_{py}] \cdot S_1(S_{roll})[R_{roll}]$$

where $S_1(s)[R]$ represents uniform scaling of the rotation "R" by a factor "s".

Extracting $R_{roll}$ from $({}_{neutral}{}^{world}R)^{-1}R_{orientation}$ takes into account the orientation of an axis of the input handle 46 and scales the roll with respect to the axis of the input handle 46. The $R_{py}$ is scaled relative to the neutral orientation taking into account that by calculating $R_{py}$ by removing the extracted $R_{roll}$ depends on the direction of the input handle 46 or the roll axis "R" of the handle (FIG. 2) so that the scaled orientation is dependent both on the neutral orientation and the roll axis "R" of the handle.

It may be beneficial to perform an axis specific orientation as a single operation. Such method of using a single operation is described herein in accordance with the present disclosure that calculates a physical orientation that would correspond to a scaled orientation. From this single operation, feedback may be provided to a clinician to represent errors in the scaled orientation or when constraints are reached due to a reduced degree of freedom of the tool 20 (i.e., approaching or reaching a singularity) or reaching an edge of the workspace. The single operation would be an inverse to be accurate in all orientations. Specifically, the aliasing should be accounted for in each of the scaled rotations.

The single operation would avoids decomposition, as described above, and combines the scaling that scales rotations about the roll axis by a scaling factor $S_{roll}$, scales rotations with no roll component by a different scaling factor $S_{py}$, and handles intermediate rotations in a manner in between. Such a scaled rotation can be represented as:

$$R_{scaled} = {}_{neutral}{}^{world}R \cdot S_2({}^{neutral}u_{roll}, S_{roll}, S_{py})[{}_{neutral}{}^{world}R]$$

Where ${}_{neutral}{}^{world}R = ({}_{neutral}{}^{world}R)^{-1}R_{orientation}$ is the overall rotation away from the neutral orientation and $S_2({}^{neutral}u_{roll}, S_{roll}, S_{py})[{}_{neutral}{}^{world}R]$ is the combined scaling operator that is derived as describe below. It should be noted that $S_2$ depends on the $S_{roll}$ and $S_{py}$ scaling factors and on the direction of the roll axis ${}^{neutral}u_{roll}$ with respect to the neutral frame.

Another method of using anisotropic scaling to calculate a scaled orientation of the tool 20 is described in accordance with the present disclosure. The anisotropic scaling scales behavior of the input handle 46 by three parameters in addition to an input rotation. The first parameter is the fixed axis "w" where (|w|=1) (i.e., the roll axis "R" detailed above), the second parameter is scaling factor $s_0$, and the third parameter is scaling factor $s_w$. The scaling factor $s_0$ and the scaling factor $s_w$ may be equal to one another or different from one another. Rotation about the axis "w" is scaled by the scaling factor $S_w$ and rotation about any axis perpendicular to the axis "w" (i.e., axis v⊥w, |v|=1) is scaled by the scaling factor $S_0$. For the anisotropic scaling to be accurate it should satisfy the following conditions: first, that rotation about the axis "w" or rotation about any axis perpendicular to the axis "w" is accurately scaled by either scaling factor $S_0$ or scaling factor $S_w$ respectively; second, that rotation about any intermediate axis is scaled by a factor between scaling factors $s_0$ and $s_w$; and third, that when $s_0 = s_w$ the scaling corresponds to an isotropic rotation scaling.

To anisotropically scale the behavior of the input handle 46, the operator $S_2$, which is inspired by the Householder Transform for Reflections, is applied to the Euler rotation vector "R" detailed above such that the rotation vector "r" is expressed as follows:

$$S_2(w, s_w, s_0)[r] = (s_0I + (s_w - s_0)ww^T)AA[R2r[R]]$$

where r2 R[r] is the conversion of an Euler rotation vector "R" to a rotation matrix, R2r[R] is the conversion of a rotation matrix "R" to an Euler rotation vector, and AA[r]

removes aliasing from a rotation vector "R" by changing the magnitude of the rotation vector "R" by some multiple of $2\pi$.

The verification of the anisotropic scaling is accurate in the conditions detailed above are described below. In a first condition, $S_2 \lambda w = s_w \lambda w$ and $S_2 \mu v$, since $w^T w = 1$ and $w^T v = 0$. In the second condition for rotation that is neither about the axis "w" nor independent of axis "w", the rotation axis may change direction (i.e., if $s_w \rangle s_0$, the axis moves away from the "v" plane towards ±w; or in the opposite direction) and the rotation angle is scaled by a factor between $s_0$ and $s_w$. Finally, when the scaling factor $s_0 = s_w$, then $S_2$ (w, $s_w$, $s_0$)=$s_0$I, to satisfies the third condition.

The inverse for the final transform for the anisotropic scaling can be calculated as follows:

$$S_2\left(w, \frac{1}{s_w}, \frac{1}{s_0}\right) S_2(w, s_w, s_0) =$$
$$\left(\frac{1}{s_0}I + \left(\frac{1}{s_w} - \frac{1}{s_0}\right) ww^T\right)(s_0 I + (s_w - s_0) ww^T) = \frac{1}{s_0} s_0 I + \frac{1}{s_0}(s_w - s_0) ww^T +$$
$$\left(\frac{1}{s_w} - \frac{1}{s_0}\right) s_0 ww^T + \left(\frac{1}{s_w} - \frac{1}{s_0}\right)(s_w - s_0) ww^T ww^T =$$
$$I + \left(\frac{s_w}{s_0} - \frac{s_0}{s_0} + \frac{s_0}{s_w} - \frac{s_0}{s_0} + \frac{s_w}{s_w} - \frac{s_0}{s_w} - \frac{s_w}{s_0} + \frac{s_0}{s_0}\right) ww^T =$$
$$I + \left(\frac{s_w}{s_0} - 1 + \frac{s_0}{s_w} - 1 + 1 - \frac{s_0}{s_w} - \frac{s_w}{s_0} + 1\right) ww^T = I$$

When the axis "w" is variable, vector operations can be used to calculate $S_2 x = s_0 x + (s_w - s_0)(w^T x) w$. For example, the vector operations can be [10*,5+] then to recompute [27*, 9+] and use [9*,6+] as the operator matrix. By using the vector operations as in place of the trigonometry may reduce the cost and/or time of performing the above anisotropic scaling method.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A robotic surgical system comprising:
    a linkage moveably supporting a surgical tool relative to a base;
    an input device rotatable about a first axis of rotation, the input device being rotatable from an idle position in a first input direction about the first axis of rotation towards a first rotated position; and
    a processing unit in communication with the input device and operatively associated with the linkage to rotate the surgical tool about a first axis of movement in a first output direction when the input device is rotated from the idle position towards the first rotated position and to maintain a radial position of the surgical tool about the first axis of movement when the input device is in the idle position.

2. The robotic surgical system according to claim 1, wherein the processing unit varies a radial speed of the surgical tool about the first axis of movement based on an amount of rotation of the input device from the idle position towards the first rotated position.

3. The robotic surgical system according to claim 2, wherein the processing unit varies the radial speed of the surgical tool about the first axis of movement in at least one of a smooth manner or a stepped manner.

4. The robotic surgical system according to claim 1, wherein the input device is rotatable about the first axis of rotation in a second direction opposite the first direction towards a second rotated position, and wherein the processing unit is operatively associated with the linkage to rotate the surgical tool about the first axis of movement in a second output direction opposite the first output direction when the input device is rotated from the idle position towards the second rotated position.

5. The robotic surgical system according to claim 1, wherein the input device is rotatable about a second axis of rotation, and wherein the processing unit is operatively associated with the linkage to rotate the surgical tool about a second axis of movement based on a scaled rotation of the input device about the second axis of rotation by a first scaling factor.

6. The robotic surgical system according to claim 5, wherein the input device is rotatable about a third axis of rotation, and wherein the processing unit is operatively associated with the linkage to rotate the surgical tool about a third axis of movement based on a scaled rotation of the input device about the third axis of rotation by a second scaling factor.

7. The robotic surgical system according to claim 6, wherein the first scaling factor is different from the second scaling factor.

* * * * *